(12) United States Patent
Sack et al.

(10) Patent No.: US 7,638,271 B2
(45) Date of Patent: Dec. 29, 2009

(54) USE OF ANTIBODY FROM LYMPHOCYTE SECRETIONS TO DIAGNOSE ACTIVE INFECTION

(75) Inventors: David A. Sack, Timonium, MD (US); Rubhana Raquib, Dhaka (BD)

(73) Assignee: ICDDR, B: The Center for Health and Population Research, Mohakhali Dhaka (BD)

( * ) Notice: Subject to any disclaimer, the term of this patent is extended or adjusted under 35 U.S.C. 154(b) by 0 days.

(21) Appl. No.: 10/903,855

(22) Filed: Aug. 2, 2004

(65) Prior Publication Data

US 2005/0089942 A1    Apr. 28, 2005

Related U.S. Application Data

(60) Provisional application No. 60/491,255, filed on Jul. 31, 2003.

(51) Int. Cl.
*C12Q 1/00* (2006.01)
*A61K 39/04* (2006.01)

(52) U.S. Cl. .............................. 435/4; 424/9.1; 424/9.2; 424/130.1; 424/164.1; 424/234.1; 424/248.1; 435/7.1; 435/29; 435/40.5

(58) Field of Classification Search .................. 424/9.1, 424/9.2, 130.1, 164.1, 234.1, 248.1; 435/4, 435/7.1, 29, 40.5
See application file for complete search history.

(56) References Cited

U.S. PATENT DOCUMENTS

| | | | | |
|---|---|---|---|---|
| 5,352,580 | A | * | 10/1994 | Spears et al. .................... 435/6 |
| 5,478,726 | A | * | 12/1995 | Shinnick et al. ............ 435/7.24 |
| 5,494,799 | A | * | 2/1996 | Wood et al. ................. 435/7.32 |
| 6,120,776 | A | * | 9/2000 | Hasløv et al. ............ 424/248.1 |

FOREIGN PATENT DOCUMENTS

WO    WO99/30162    *    6/1999

OTHER PUBLICATIONS

Franco Ameglio, MD. et al., "Use of Discriminant Analysis to Assess Disease Activity in Pulmonary Tuberculosis with a Panel of Specific and Nonspecific Serum Markers," American Journal Clinical Pathology, Rome, Italy, Jun. 1994, vol. 101, No. 6, pp. 719-725.
C. Saltini et al., "Soluble Immunological Markers of Disease Activity in Tuberculosis," European Respiratory Journal, 1999, pp. 485-486.
Sudha Pottumarthy et al., "Evaluation of the Tuberculin Gamma Interferon Assay: Potential to Replace the Mantoux Skin Test," Journal of Clinical Microbiology, vol. 37, No. 10, pp. 3229-3232.
M. S. Al-Hajjaj et al., "Improved Sensitivity for Detection of Tuberculosis Cases by a Modified Anda-TB ELISA Test," Tubercle and Lung Disease, 1999, vol. 79, No. 3, pp. 181-185.
A. Yilmaz et al., "The Value of Ca 125 in the Evaluation of Tuberculosis Activity," Respiratoy Medicine, 2001, vol. 95, pp. 666-669.

Robin E. Huebner et al., "Tuberculosis Commentary," Clinical Infectious Diseases, 1993, vol. 17, pp. 968-975.
Paul E. M. Fine et al., "Delayed-Type hypersensitivity, Mycobacterial Vaccines and Protective Immunity," The Lancet, Nov. 5, 1994, vol. 344, pp. 1245-1249.
R. Dhand et al., "False-Positive Reactions with Enzyme-Linked Immunosorbent Assay of Mycobacterium Tuberculosis Antigens in Pleural Fluid," Journal of Medical Microbiology, vol. 26, issue 4, p. 241 (abstract).
Wang CR et al., "Enzyme-linked Immunosorbent Assay with BCG Sonicate Antigen for Diagnostic Potential of Mycobacterial Infection in Taiwan," National Library of Medicine, Zhonghua Min Guo Wei Sheng Wu Ji Mian Yi Xue Za Zhi, May 1989, vol. 22, No. 2, p. 97 (abstract).
A. Aoki et al. "Their Tilters and Recognized Molecules of IgG Class Anti-BCG Antibody in Sera from Patients with Tuberculosis," National Library of Medicine, Nihon Kyobu Shikkan Gakkai Zasshi, May 1990, pp. 729-735 (abstract).
N. Banchuin et al., "Value of an ELISA for Mycobacterial Antigen Detection as a Routine Diagnostic Test of Pulmonary Tuberculosis," National Library of Medicine, Asian Pac J Allergy Immunol., Jun. 1990, p. 5 (abstract).
Chuan-Zhen Lu et al., "Early Diagnosis of Tuberculous Meningitis by Detection of Anti-BCG Secreting Cells in Cerebrospinal Fluid," The Lancet, Jul. 1990, vol. 336, pp. 10-14.
Sandra M. Arend et al. "Detection of Active Tuberculosis Infection by T Cell Responses to Early-Secreted Antigenic Target 6-kDa Protein and Culture Filtrate Protein 10," The Journal of Infectious Diseases, 2000, vol. 181, pp. 1850-1854.
John M. Pollock et al., "The Potential of the ESAT-6 Antigen Secreted by Virulent Mycobacteria for Specific Diagnosis of Tuberculosis," Journal of Infectious Diseases, 1997, vol. 175, pp. 1251-1254.
Laurens A. H. van Pinxteren et al., "Diagnosis of Tuberculosis Based on the Two Specific Antigens ESAT-6 and CFP10," Clinical and Diagnostic Laboratory Immunology, Mar. 2000, vol. 7, pp. 155-160.
J.M. Querol et al., "Usefulness of IgG and IgM Detection Against Antigen 60 in the Diagnosis of Thoracic Tuberculosis," National Library of Medicine, An Med. Intern., Jun. 1993, vol. 10, p. 271 (abstract).
S.M. Qadri et al., "Nonspecificity of the Anda A60-tb ELISA Test for Serodiagnosis of Mycobacterial Disease," National Library of Medicine, Can J Microbiol, Aug. 1992, vol. 8, p. 804 (abstract).
R.F. Maes, "Evaluation of the Avidity of IgG Anti-Mycobacterial Antibodies in Tuberculous Patients Serum by an A-60 Immunoassay." National Library of Medicine, Euro J. Epidemiol, Mar. 1991, vol. 7, pp. 188-190 (abstract).
C. Delacourt et al., "Value of ELISA Using Antigen 60 for the Diagnosis of Tuberculosis in Children," Chest, 1993, vol. 104, p. 393 (abstract).

(Continued)

*Primary Examiner*—Rodney P. Swartz
(74) *Attorney, Agent, or Firm*—Venable LLP; Ann S. Hobbs

(57) ABSTRACT

A method and kit for the detection of an infectious disease, particularly tuberculosis, wherein lymphocytes of a subject are incubated with a disease-specific antigen, and the level of antibody production is measured, the production of antibodies above a baseline level being indicative of infection.

10 Claims, 6 Drawing Sheets

OTHER PUBLICATIONS

M. Turneer et at., "Determination of Humoral Immunoglobulins M and G Directed Against Mycobacterial Antigen 60 Failed to Diagnose Primary Tuberculosis and Mycobacterial Adenitis in Children," American Journal of Respiratory and Critical Care Medicine, Dec. 1994, vol. 150, No. 6, p. 1508 (abstract).

Johan Vekemans et al., "Tuberculosis Contacts but Not Patients have Higher Gamma Interferon Responses to ESAT-6 than Do Community Controls in The Gambia," Infection and Immunity, Oct. 2001, vol. 69, pp. 6554-6557.

Konstantin Ly Ashchenko et al., "Heterogeneous Antibody Responses in Tuberculosis," Infection and Immunity, Aug. 1998, vol. 66, pp. 3936-3940.

H. Sunny Chang et al., "Development of a Novel in Vitro Assay (ALS Assay) for Evaluation of Vaccine-Induced Antibody Secretion from Circulating Mucosal Lymphocytes," Clinical and Diagnostic Laboratory Immunology, May 2001, vol. 8, No. 3, pp. 482-488.

A. O. Sousa et al., "Kinetics of Circulating Antibodies, Immune Complex and Specific Antibody-Secreting Cells in Tuberculosis Patients During 6 Months of Antimicrobial Therapy," Tubercle and Lung Disease, 2000, vol. 80, No. 1, pp. 27-33.

Rubhana Raqib et al., "Rapid Diagnosis of Active Tuberculosis by Detecting Antibodies from Lymphocyte Secretions," J. Infect. Dis., Aug. 2003, vol. 188, pp. 364-370.

Rubhana Raqib et at., "Use of Antibodies in Lymphocyte Secretions for Detection of Subclinical Tuberculosis Infection in Asymptomatic Contacts," Clinical and Diagnostic Laboratory Immunology, Nov. 2004, vol 11, No. 6, pp. 1022-1027.

* cited by examiner

USE OF ANTIBODY FROM LYMPHOCYTE SECRETIONS TO DIAGNOSE ACTIVE INFECTION

This application claims priority to U.S. provisional application No. 60/491,255, filed Jul. 31, 2003, the entire contents of which are incorporated herein by reference.

BACKGROUND OF THE INVENTION

1. Field of the Invention

The invention relates to a method of diagnosing tuberculosis by culturing lymphocytes from a subject to produce antibodies, and measuring the concentration of antibodies reactive with a tuberculosis antigen.

2. Background Information

Tuberculosis (TB) remains a major global health problem and is the most frequent cause of death from a single infectious agent [1]. The appearance of multidrug-resistant strains of *Mycobacterium tuberculosis* and the HIV/AIDS epidemic have contributed to the resurgence of active TB in humans. Thus, WHO declared tuberculosis a global emergency in 1993. Surveys carried out in Bangladesh from 1987 to the present suggest the smear positive TB case rate in Bangladesh to be between 1-1.8% [2-5].

Early diagnosis of TB is crucial to prevent the spread of the disease in the community. However, the clinical and laboratory diagnosis, follow-up of the infection activity and response to the therapy is not always easy to evaluate [6, 7]. Although, culture of bacteria is the gold standard in diagnosis and follow-up of disease, it can take up to 6-8 weeks to isolate *M. tuberculosis*. It is estimated that a false negative culture result may be obtained in 10-20% of TB cases [8, 9]. A rapid serological test for diagnosis, follow-up of disease activity and response to therapy would be very useful to the clinicians [10, 11]. The PPD skin test (Mantoux test) is an important tool for diagnosis of latent TB infection and disease in the developed world but it has low predictive value in Bacillus-Calmette-Guerin (BCG)-vaccinated individuals as well as in individuals living in areas endemic for TB due to cross-reactivity with BCG and atypical mycobacteria, and false negative reactions in malnourished children [12-14].

BCG has been used as an antigen in enzyme immunoassays in in vitro studies to determine the disease activity but was aborted due to difficulties in interpretation, or differentiating between active or past disease, and low sensitivity and specificity, respectively [15-19]. With the identification of regions of *M. tuberculosis* genome that are missing in BCG and nontuberculous mycobacterium, new antigens have been identified providing better opportunities for development of novel diagnostic tools [20-22]. The introduction of these antigens resulted in a much higher sensitivity and specificity in cell response assays [23]. However, serological tests based on mycobacterial antigens to detect circulating antibodies have been hampered by decreased sensitivity and cross-reactivity with other mycobacteria [24-28] or have relatively limited utility in the diagnosis of tuberculosis in countries where tuberculosis is endemic [29]. Several molecular biological techniques have been proposed as indicators of disease activity in pulmonary and extrapulmonary tuberculosis [30, 31] and are currently the most sensitive and specific diagnostic tests. However, a recent study on inter-laboratory comparisons of PCR-based TB diagnosis have demonstrated the complications of obtaining reproducible results with such sensitive techniques where false positive results can be a major problem [32].

The diagnosis of tuberculosis is currently made using one of several methods: 1) a positive culture for tuberculosis from a sputum or other biological sample, 2) a positive smear of sputum in which typical tuberculosis organisms are seen microscopically, 3) a positive histological examination of tissue from the patient, 4) a positive skin test (PPD) in a patient with a clinical examination suggestive of tuberculosis.

These methods suffer from a number of drawbacks. First, culture methods are time consuming, generally taking several weeks to perform. In addition, if the amount of sample being tested is insufficient, they result in substantial numbers of false negatives. The sputum smear suffers from poor sensitivity. The histological examination requires an invasive procedure and is generally only performed in the case of extrapulmonary tuberculosis. The skin test results in many false positive and false negative reactions; furthermore, a positive result does not distinguish between active disease, inactive infection, prior immunization with BCG vaccine, or exposure to similar organism(s).

Although a number of blood tests have been explored in attempts to overcome these problems, all have suffered from a lack of sensitivity and specificity. Thus, there is a need for a test that will more rapidly detect tuberculosis infection, and that will distinguish active disease from inactive disease, BCG vaccination, and exposure to similar organisms.

In vitro assay of antibody secretion by lymphocytes ("ALS assay") has been previously used to measure postvaccination immunity following cholera vaccination [33] but has not been used for the detection of active infection, in particular active tuberculosis infection. In the present invention we demonstrate the diagnostic potential of tuberculosis-specific ALS responses in Bangladeshi subjects for the assessment of active pulmonary tuberculosis and detection of infection in exposed symptom-free contacts of TB index cases.

SUMMARY OF THE INVENTION

The present invention provides a method for the detection of active infection with tuberculosis and other infectious diseases that makes use of antibodies produced in vitro by lymphocytes from peripheral blood. This method can also be used for identifying subclinical TB infection in asymptomatic contacts of TB index cases that later progress to active TB.

The method uses a sample of blood of a patient suspected of having a specific infectious disease (e.g. tuberculosis). Lymphocytes from the patient sample are separated from other blood cells and are cultured under suitable conditions, following which the concentration of antibodies specific for the infectious disease present in the culture medium are measured.

Culture of the lymphocytes can be carried out for a suitable time period to obtain a measurable concentration of antibodies specific for the suspected disease, compared to a baseline ("0") value measured in normal control subjects. In the case of tuberculosis, a period of 1-5 days, preferably 3 days, has been found to be suitable. A skilled practitioner will be able to determine other suitable time-periods for tuberculosis and other diseases using routine experimentation. Antibody concentrations can be determined by measuring the amount of antibody bound to an antigen specific for the microorganism causing a particular disease using methods that are known in the art, for example, Enzyme-linked Immunosorbent Assay (ELISA).

In an alternative embodiment of the invention, other known methods of detecting antibody production in circulating lymphocytes, or counting the numbers of antibody secreting cells, can be used. For example, the cells may be enumerated using methods such as Enzyme-linked Immunospot (ELISPOT) or may be labeled using fluorescent labeled antibody and counted using a Fluorescence Activating Cell Sorter. To measure the number of antibody producing cells using fluorescent labeled antibody, it is assumed that the antibody for the disease of interest (e.g. an antituberculosis antibody) is located on the surface of the lymphocyte. After separation from the other cells (as in the ALS assay), the lymphocytes are mixed and incubated with antigen (e.g. BCG, PPD, early secretory antigenic target-6 (ESAT-6), lipoarabinomannan (LAM), culture-filtrate protein (CFP) or other suitable tuberculosis antigen for a suitable period (e.g one hour). The cells are then washed to remove any unbound antigen, and mixed and incubated with a fluorescent labeled antibody to the disease of interest (e.g. a labeled antituberculosis antibody). This labeled antibody will only bind to the cells that have already bound the tuberculosis antigen. The concentration of these cells can then be determined by counting the fluorescent cells using a fluorescent activated cell sorter or a fluorescent microscope.

In the case of tuberculosis BCG, PPD, ESAT-6, LAM, CFP and other crude or purified antigens that are representative of tuberculosis bacteria can be used. The amount of antibody secreted by the lymphocytes of the test subject (or the number of actively secreting lymphocytes) is compared to the amount secreted by a normal (control) subject, who is known to be uninfected. Antibody production may also be compared with that of subjects who have received BCG vaccine. An increase in the titer of antibody in the patients above that of the control subjects is indicative of active tuberculosis infection. The amount of the increase above that of the controls is determined by statistical analysis such that the titers of groups of subjects with infection is statistically higher than the titers of groups of control subjects. Suitable standard curves can be run to establish antibody levels that are indicative of active infection for other diseases and antigens, using control subjects and subjects that are known to be actively infected.

Culture conditions for lymphocytes are familiar to those skilled in the art and are described in the attached manuscript. Typical steps in the lymphocyte culture methods include separating the lymphocytes from the other cells in the blood, adjusting the cell concentrations to a standard number of cells per milliliter, and culturing them in a suitable tissue culture medium in an incubator at about 37° C. with a 5% $CO_2$ atmosphere.

Other diseases for which the method should be particularly suitable are other chronic infections such as chronic fungal infections (e.g. coccidiomycosis, histoplasmosis) chronic bacterial infections (e.g. *Helicobactor pylori*), chronic parasitic infection (e.g. visceral leishmaniasis). These infections, like tuberculosis, may also result in inactive infections and active infections, and the test is expected to help distinguish active from inactive infection.

Accordingly, in one embodiment, the invention provides a method of diagnosing tuberculosis in a subject comprising culturing lymphocytes from said subject under suitable conditions such that antibodies are produced, and measuring the concentration of antibodies reactive with a tuberculosis antigen, wherein an increase in said concentration over a normal control sample is indicative of active tuberculosis infection. Control samples representing known positive and negative samples, can be included for quality control purposes. From a baseline value determined for the control samples, a cutoff point for the diagnosis of infection will generally be selected that represents a value that has been predetermined by testing control and patient populations or which is in the best judgment of the practitioner the level of antibody at which a positive diagnosis can be made, e.g. 10% above control, 20% above control, etc., depending on the patient population and the experience of the practitioner. Preferably, the lymphocytes are cultured for 1-5 days, more preferably for 2-4 days. In one preferred embodiment, the lymphocytes are separated from other blood cells prior to culture.

The tuberculosis antigen used for this aspect of the invention may be any antigen that is specific for tuberculosis and that is capable of eliciting antibody production from lymphocytes under suitable culture conditions. Preferably, the antigen is selected from the group consisting of BCG, PPD, ESAT-6, LAM and CFP.

The invention also includes a method of diagnosing tuberculosis in a subject comprising
  i) obtaining a blood sample from said subject;
  ii) separating lymphocytes from the sample;
  iii) culturing the lymphocytes in a culture medium under suitable conditions;
  iv) measuring the concentration of antibodies reactive with a tuberculosis antigen in said medium;
  wherein an increase in said concentration over a normal control sample is indicative of active tuberculosis infection.

Preferably, the antigen is selected from the group consisting of BCG, PPD, ESAT-6, LAM and CFP.

The assay also enables detection of infection in exposed, symptom-free contacts, which are at greater risk of developing active TB. The potential applications of the ALS assay would include evaluation of recent TB contacts in countries with high TB rates and in industrialized countries for contact tracing as well as for screening of immigrants from TB endemic countries.

In particularly preferred embodiments of the methods of the invention, antibodies are detected using ELISA or an immunochromatographic method. The concentration of antibody-producing lymphocytes in the peripheral blood may be measured using ELISPOT or by tagging the lymphocytes with a detectable marker, such as a radioisotopically labeled or fluorescent labeled antibody.

The invention also includes a method of diagnosing active infection in a subject comprising culturing lymphocytes from said subject under suitable conditions such that antibodies are produced and measuring the concentration of antibodies reactive with a target disease antigen, wherein an increase in said concentration over a normal control sample is indicative of active infection with the target disease. In one preferred embodiment of this aspect of the invention, the target disease is a chronic infection, such as, for example, tuberculosis, coccidiomycosis, histoplasmosis, *Helicobactor pylori*, or visceral leishmaniasis.

The lymphocytes are cultured for a suitable time period necessary for antibody production, generally 1-5 days, more preferably 2-4 days. Preferably, the lymphocytes are separated from other blood cells prior to culture.

The invention also includes a method of diagnosing active infection of a target disease in a subject, said method comprising measuring the number of lymphocytes present in a blood sample obtained from said subject that secret antibodies reactive with a specific target disease antigen, wherein an increase in said number over a normal control sample is indicative of active infection with the target disease. In one preferred embodiment of this aspect of the invention, the target disease is a chronic infection, for example, tuberculosis, coccidiomycosis, or histoplasmosis, *Helicobactor pylori*, or visceral leishmaniasis.

The invention also includes a kit for carrying out the methods of the invention, the kit comprising a suitable antigen specific for the disease to be detected, and optionally reagents needed for culturing lymphocytes and detecting any resulting antibodies. The kit might also include reagents for carrying out suitable baseline and/or control samples. Assuming that the laboratory to be conducting the test would have basic laboratory supplies and equipment such as a $CO_2$ incubator, centrifuge, ELISA reader, plastics, etc, the kit for the detection of tuberculosis might include, for example:

1. A tube for collecting a blood sample and reagents/supplies for separating lymphocytes (mononuclear cells), or a Vacutainer™ CPT™ tube (Becton Dickinson) single tube system for collection of whole blood and separation of mononuclear cells
2. Tube(s) or plate for culturing the lymphocytes
3. Tissue culture media for maintaining the lymphocytes in culture for up to 5 days.
4. A vial for holding the tissue culture media after the lymphocytes have been incubated, (e.g. microfuge tubes or cryovials)
5. A microtiter plate coated with TB antigen for carrying out the ELISA reaction
6. control reagents which known to give positive and negative reactions as quality control standards
7. Enzyme labeled antibody for the ELISA test
8. Substrate for the ELISA test
9. Buffers for the ELISA test Although the inventors do not intend to be bound by any particular theory, it is believed that active infection results in constant stimulation of antibody-producing cells and that this stimulation results in constant circulation of antibody-producing cells in the peripheral blood. In contrast, old inactive infection or prior vaccination may result in high antibody serum titers, but not in constant stimulation, thus there will be few antibody-producing cells circulating in the peripheral blood.

References cited herein are hereby incorporated by reference.

DETAILED DESCRIPTION OF THE INVENTION

Materials and Methods

Figure 1:
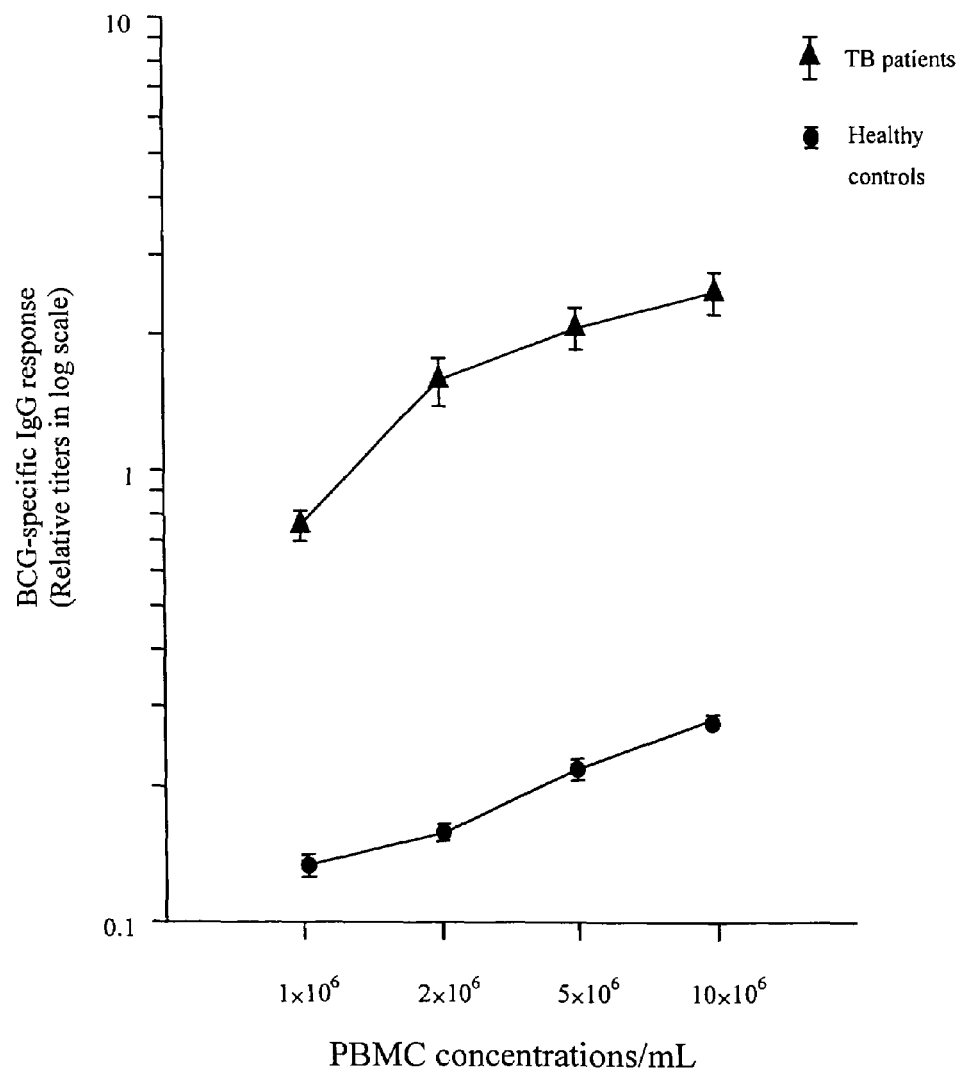
FIG. 1. Comparison of BCG-specific IgG responses (relative titers) in lymphocyte secretions at various cell concentrations in patients and healthy controls. Each point represents average titers of BCG-specific IgG with standard error of mean (±SE). Significantly higher BCG-specific IgG titers were obtained at higher cell concentrations ($2-10\times10^6$ cells/mL) compared to $1\times10^6$ cells/mL (P<0.001). Healthy controls had consistently low BCG-specific IgG titers at all cell concentrations.

Study Subjects and Sampling.

Adult patients with suspected pulmonary tuberculosis from the National Institute of Diseases of the Chest and Hospital (NIDCH) in Dhaka, Bangladesh were prospectively studied. The diagnosis of tuberculosis was established by the clinical presentation, chest X-ray examination and sputum smear positivity. Clinical evaluation included lung opacity, pyrexia, weight loss, high erythrocyte sedimentation rate (ESR) and positive sputum smear. Sputum was collected twice on consecutive days for mycobacterial culture from each patient after enrollment. Diagnosis was further confirmed when sputum culture was found to be positive. All patients received standard therapy that included rifampicin, isoniazid, pyrazinamide and ethambutol. Most of these patients had been ill for 3-5 months prior to inclusion in the study. Tuberculin skin test was not performed in these patients since in Bangladesh BCG is given to about 80% of people, exposure to environmental mycobacteria is considered to be widespread and incidence of tuberculosis infection is high rendering the skin test less specific [5, 34, 35). The history and inspection for typical scar included detecting a scar resulting from previous vaccination with M. bovis BCG. Although it is also possible that some patients may not develop a scar after vaccination and may be falsely grouped as non-vaccinated, most of these patients were however able to tell whether they were vaccinated or not with the exception of two who were unsure of their vaccination status and did not have the scars. They were grouped as non-vaccinated.

Patients attending the hospital with symptoms suggestive of tuberculosis with lung opacity, high ESR but sputum smear negative and culture negative were enrolled as non-tuberculosis patients. Healthy laboratory personnel (with no known exposure to M. tuberculosis) were also selected as healthy controls. Tuberculin skin test was performed on these healthy controls only. Blood was collected from each patient at enrollment with <4 weeks of antimycobacterial drug treatment. In addition, blood was also collected from the non-tuberculosis patients and healthy subjects. The study was approved by the ethical review committee of the International Centre for Diarrhoeal Disease Research, Bangladesh (ICD-DR,B): International Center for Health and Population Research in Dhaka. Signed informed consent was obtained from each study subject according to the guidelines of the ethical review committee.

Sputum Culture

Sputum from patients were collected at the NIDCH and were cultured for M. tuberculosis at the ICDDR,B on Lowenstein Jensen medium using standard culture techniques.

Antibodies from Lymphocyte Secretions (ALS).

Peripheral blood mononuclear cells (PBMC) were separated from blood upon Ficoll-Paque by differential centrifugation, and were suspended in 24-well tissue culture plates (Costar, Cambridge, Mass.) in RPMI 1640 culture medium (GIBCO BRL, Grand Island, N.Y.) containing 10% fetal bovine serum (GIBCO), 2 mM L-glutamine and 1% amphotericin B-penicillin-streptomycin-mix (Sigma Chemicals Co., St; Louis, Mo.). Different dilutions of PBMC ($1\times10^6$, $2\times10^6$, $5\times10^6$ and $1\times10^7$ cells/ml) were incubated at 37° C. with 5% $CO_2$. Culture supernatants were collected at 24, 48, 72 and 96 hours post incubation. A cocktail of protease inhibitors (4-aminoethyl benzenesulfonyl flouride, 0.2 μg/ml; Aprotinin, 1 μg/ml; Leupeptin 10 μm; sodium azide 1 mg/ml in PBS) were added to the supernatants and were stored at −70° C. until used for the assay.

Antigen-Specific IgG Antibodies in Lymphocyte Secretions.

Antigens tested for the method were BCG (Freeze-dried, glutamate-BCG vaccine for intradermal use, lot # 1861, Japan BCG Laboratories, Japan; no preservatives added, saline used as diluent), and purified protein derivative (PPD, Sigma Chemical Co, St Louis, Mo.). Antibody (IgG) titers were measured in supernatants by the enzyme-linked immunosorbant assay (ELISA). Polystyrene microtitre plates (Nunc-Maxisorp) were first coated with BCG vaccine (1 μg/well) or PPD (1 μg/well) in carbonate buffer (0.1 M sodium bicarbonate and 5 mM magnesium chloride, pH-9.8) and incubated overnight at 4° C. After washing, the plates were blocked with 10% FBS in phosphate buffered saline (PBS, pH 7.2) and incubated at 37° C. for 60 minutes. Lymphocyte supernatants were thawed and brought to room temperature. Following washing with PBS-tween, lymphocyte supernatants of appropriate dilutions (diluted in 10% FBS in PBS) were added (100 μL/well) and incubated for 2 hours at 37° C. Plates were washed and rabbit anti human IgG HRP conjugate (1:100) in PBS containing 10% FBS was added and incubated for 2 hours at room temperature. After washing, freshly prepared substrate (O-phenylenediamine (OPD; 1 mg/ml in 0.1M sodium citrate (pH-4.5) buffer and $H_2O_2$) was added and the plates were developed. The enzyme reaction was stopped with 1.0 M $H_2SO_4$ and optical density (OD) was measured after 20 min at 492 nm. Pooled sera from *M. tuberculosis* culture positive patients were used as positive control (OD>1.0). Antigen-specific responses were expressed as relative titers, which were defined as the optical density multiplied by the dilution factor of the specimen [36].

Statistical Analysis

Statistical analyses were carried out using the SigmaStat software (Jandel Scientific, San Rafael, Calif.). Comparisons between the groups were made using the One Way Analysis of Variance (ANOVA) or ANOVA on ranks as appropriate. P-values were considered significant when $\leq 0.05$. Receiver-operator characteristic (ROC) curves were constructed to describe the relation between the sensitivity and specificity at varying cutoff levels of BCG- or PPD-specific IgG titers in lymphocyte secretions (ALS).

Results

Demography of Patients

Forty-nine patients with suspected pulmonary TB were recruited from Institute of Diseases of the Chest and Hospital (IDCH). Only those patients who had two consecutive-sputum specimens positive for acid-fast bacilli (AFB) were included in the study. Out of 49 patients with smear positive pulmonary TB, 45 patients were culture positive for *M. tuberculosis* (92%) and 2 had contaminated culture and 2 were culture negative. All patients received the standard treatment and for therapy-resistant cases, the treatment was modified. Median age of the patients was 30 years with a range of 18 to 57 years. Thirty-six of forty-nine TB patients were males and thirteen were females. Among them, thirty-five were BCG vaccinated (having a BCG scar).

Patients with non-tuberculosis illness (n=35) included patients with bronchiectasis (n=22), lung cancer (n=7), lung abscess (n=4) and aspergillosis (n=2). The diagnosis was confirmed by histology or cytology. Thirty-five healthy individuals (laboratory personnel) were included in the study as healthy controls all of whom except one were BCG vaccinated.

Lymphocyte Numbers and Supernatant Dilution.

Culture supernatants from different concentrations of cell suspensions and different incubation time points were used to determine antigen-specific IgG titers. With higher concentration of PBMC, higher BCG-specific IgG titers were obtained (FIG. 1). BCG-specific IgG titers were significantly higher in supernatants of 2, 5 and 10 million cells compared to that in 1 million cells (P<0.001). For 2 to $10\times10^6$ PBMC/ml, the supernatants need to be diluted 2-4 times. However with the cell concentration of $1\times10^6$ PBMC/ml, undiluted supernatants had to be used.

Since the PBMC counts are usually low in moderate to severely sick TB patients, we opted for one million cell/ml suspensions.

BCG- and PPD-Specific Antibodies in Lymphocyte Secretions

Figure 2:
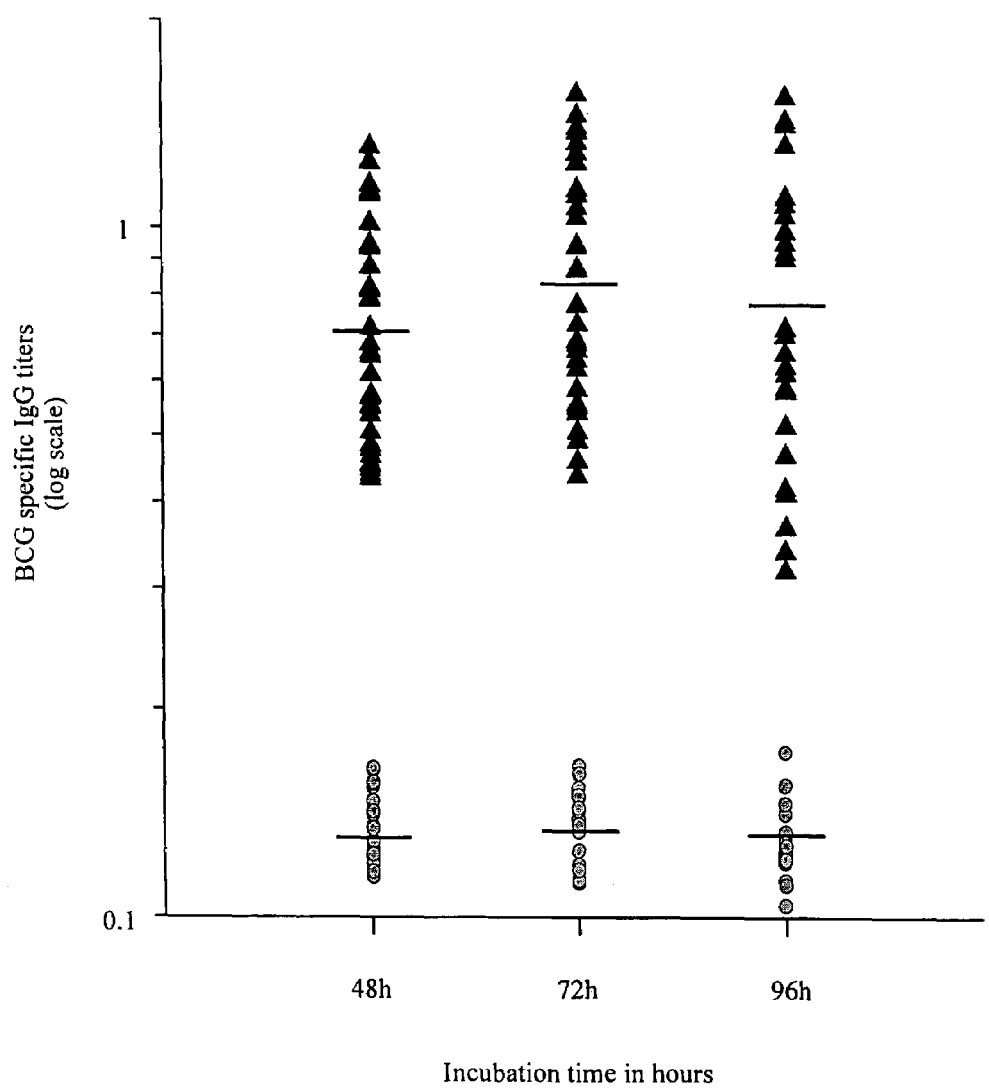
FIG. 2. Comparison of BCG-specific IgG responses (relative titers) in lymphocyte secretions at various incubation time intervals in patients and healthy controls. The horizontal bars represent geometric mean titers of specific IgG. TB patients (▲) had significantly high specific IgG titers at all time points compared to healthy controls (●) (P<0.001). Healthy controls had consistently low BCG-specific IgG titers at all incubation time points.
Figure 3:
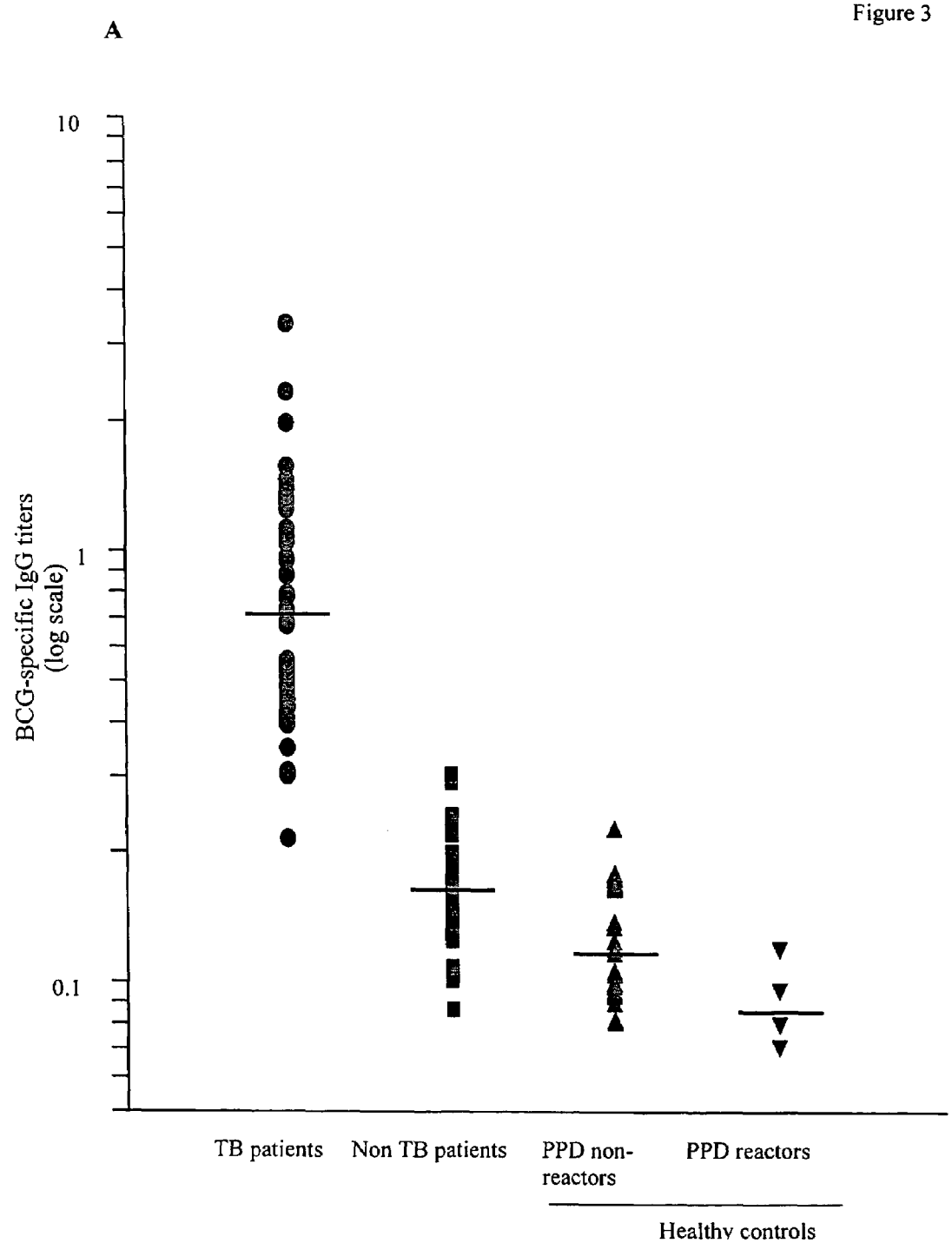
FIGS. 3A and 3B. The ALS responses to BCG (FIG. 3A) and PPD (FIG. 3B) in patients with tuberculosis (●) were significantly higher than in non-tuberculosis patients (■) and healthy controls (▲, ▼) (P<0.001). Statistical comparison between groups were performed using the ANOVA or ANOVA on ranks. Short horizontal lines represent geometric mean titers for the groups.
Figure 3:
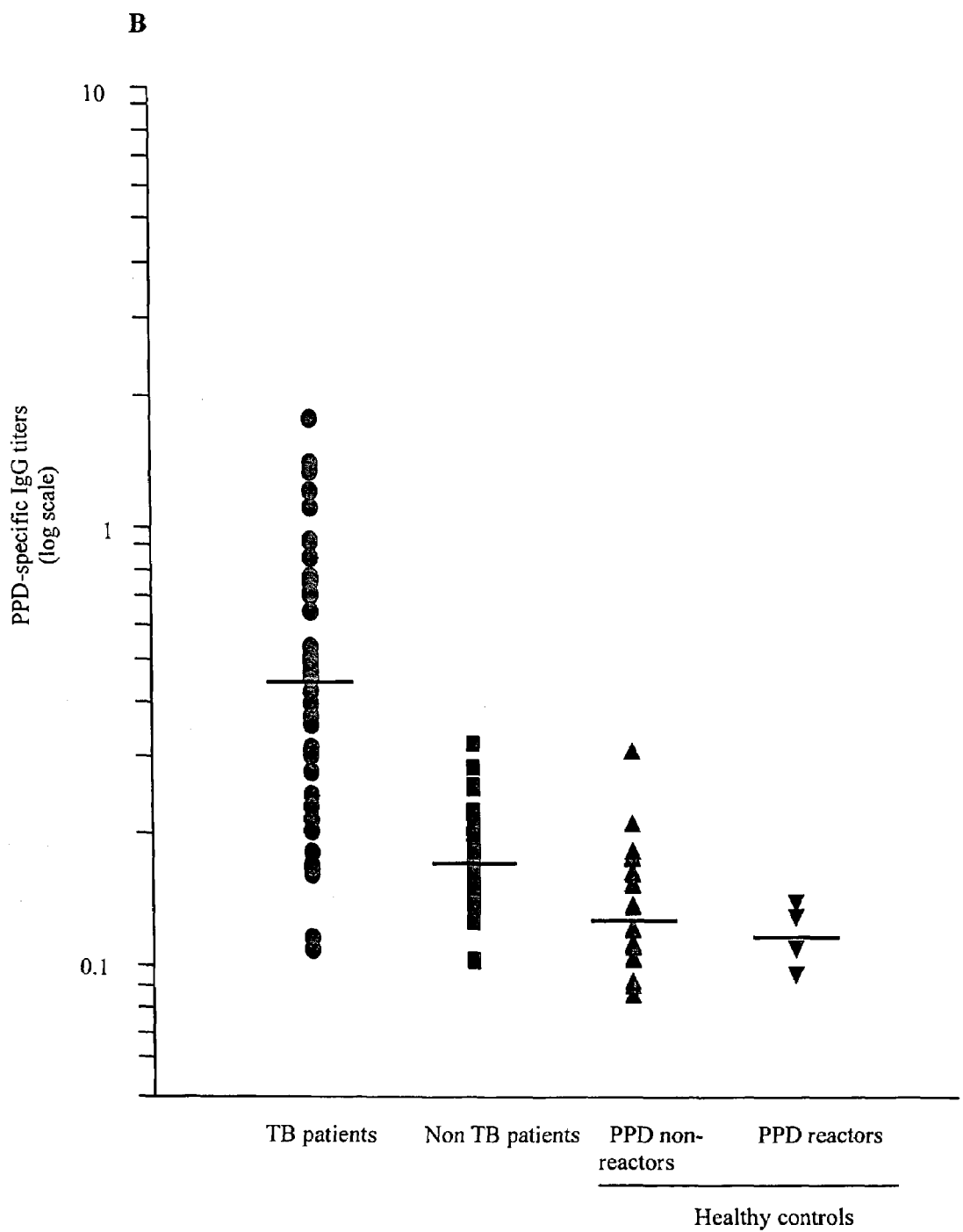

A gradual increase in relative titers of BCG-specific antibody was found from 48 to 72 hours with a slight decline in the titers at 96 hours (FIG. 2). The titers at 24 h were low and only studied in a few subjects. The optimum time point was found to be 72 hours. Pulmonary TB patients had significantly higher BCG-specific IgG antibody titers than healthy subjects (P<0.001), and non-TB patients (P<0.001) at all time points (FIG. 3A). Response to PPD (FIG. 3B) was similar to that seen with BCG-vaccine. There was no significant difference in the BCG-specific antibody titers between patients with (35 vaccinated; geometric mean (GM) of relative titer-0.67) or without BCG vaccination (14 non-vaccinated; GM=0.75) (P=0.5).

Cutoff Level to Define a Positive Test Result

Figure 4:
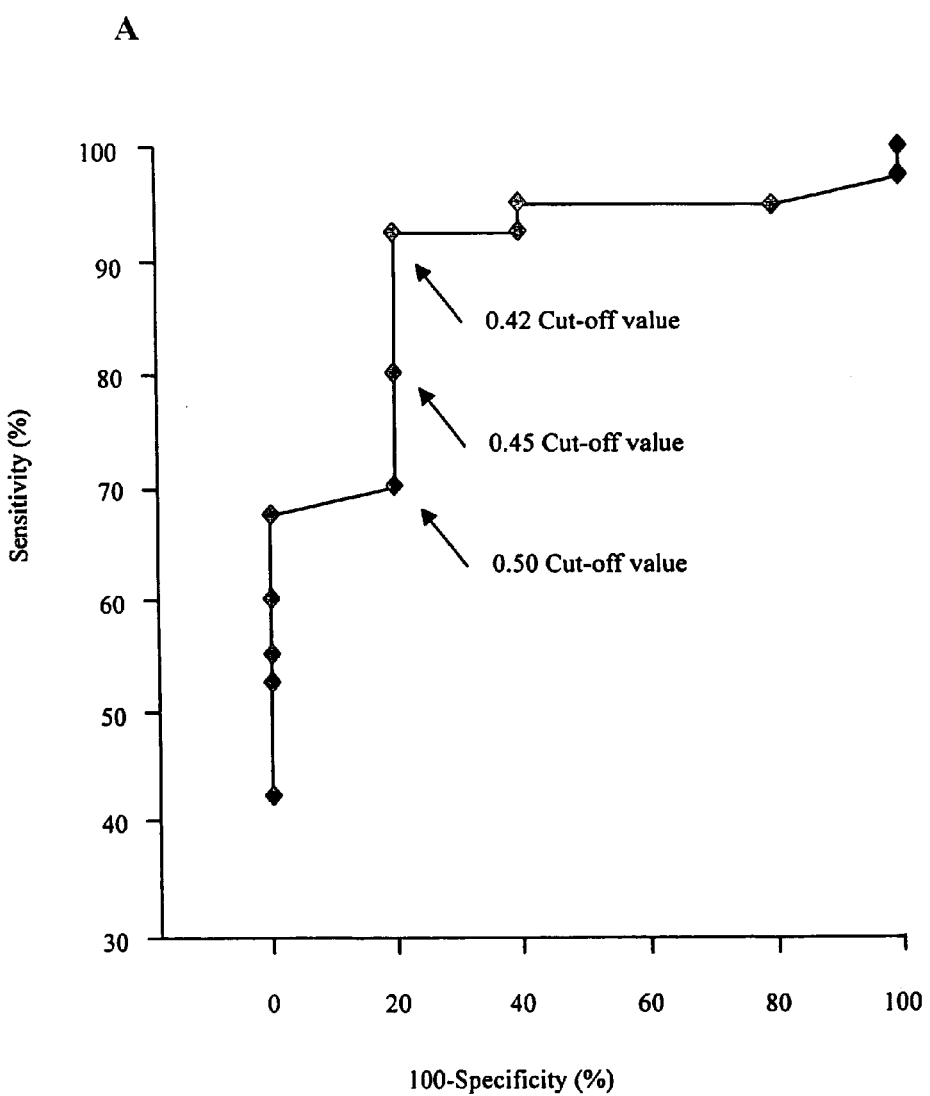
FIGS. 4A and 4B. Receiver-operator characteristic (ROC) curves were constructed from ALS responses to BCG (FIG. 4A) and PPD (FIG. 4B) in 49 tuberculosis patients and in 35 healthy controls. Some potential cutoff levels are indicated by arrows.
Figure 4:
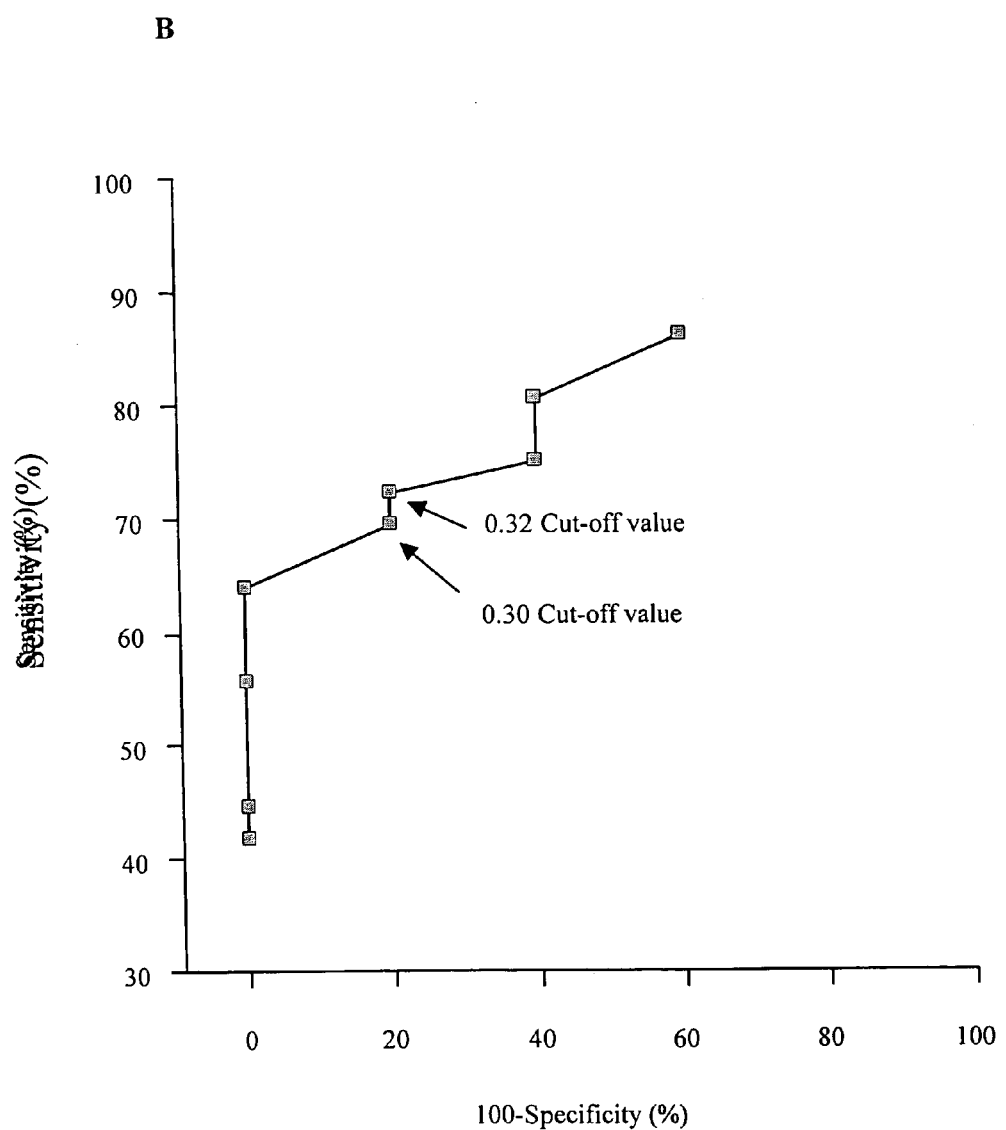

ROC curves were constructed from the ALS responses to BCG or PPD comparing TB patients with healthy controls. The selection of the best cutoff point value was based on the level at which the accuracy was maximum. The best cutoff point was found to be 0.42 with a sensitivity of 92.5% and a specificity of 80% for the BCG-ALS assay (FIG. 4A). For PPD-specific response, the best cut-off value was 0.32 with a sensitivity of 73% and a specificity of 80% for the ALS assay (F*ig*. 4B). The sensitivity and specificity for BCG-ALS assay were higher than those of PPD-specific ALS assay. The positive predictive value of the assay was 97%.

Discussion

A rapid diagnostic assay that can detect patients with active tuberculosis is urgently needed to control and prevent the spread of pulmonary tuberculosis. We report a novel technique to rapidly identify such patients by culturing peripheral blood lymphocytes and detection of tuberculosis-specific antibodies in lymphocyte secretions. Comparison between bacteriologically confirmed TB patients and non-tuberculosis patients (having illness in which TB was part of the differential diagnosis) or healthy controls showed a significant difference in the BCG antigen-specific-IgG antibody responses in the secretions. The sensitivity and specificity of the test were about 93% and 80% respectively indicating that the combination of the ALS and ELISA assays using BCG vaccine as an antigen would enable rapid detection of *M tuber-*

*culosis* infection (within 4-5 days) in patients with active tuberculosis. Prior BCG vaccination did not hamper the test for identification of TB and could successfully differentiate between BCG-vaccinated and *M. tuberculosis* infected patients. The positive predictive value of the test was 97%.

Detection of antigen specific antibody secreting cells (ASC) have been used for monitoring therapeutic responses in TB patients [37]. We evaluated the ALS technique because we hypothesized that active tuberculosis would provide continuous antigen stimulation resulting in antibody producing cells in circulation. By contrast inactive tuberculosis might result in high antibody titers in serum but would be less likely to stimulate antibody producing cells in circulation. In addition, it is easier to perform ALS assay and the supernatant can also be stored for future use to detect antigen-specific antibodies, novel antigens, cytokines and other mediators. BCG-vaccine and PPD were chosen as antigens for the easy availability and assessment of a broad spectrum of TB-specific antibodies, since they cover a vast array of protein and lipid antigens. ALS response to both BCG and PPD were similar however, the sensitivity and specificity of the BCG-specific ALS response were higher. Our ongoing follow-up study of family contacts indicates that increased ALS responses to BCG or PPD are associated with increased risk of developing active TB.

Various purified protein antigens have been tested for diagnostic applications; for example, ESAT-6, which is a small molecular weight peptide expressed by *M. tuberculosis, M. bovis* and *M. africanum* and is absent from all strains of *M. bovis* and most of the environmental mycobacteria. Recent studies have found ESAT-6 to be a highly promising antigen for immunodiagnosis of active *M. tuberculosis* infection in nonendemic regions [38-41]. However, in regions endemic for tuberculosis such as The Gambia, India and Bangladesh, contacts of TB patients had significantly higher ESAT-6 specific response than TB patients [29, 42] thereby limiting the use of the method to nonendemic countries. There is a long term persistence of ESAT-6 specific antibodies in patients in remission from pulmonary TB in endemic areas making it difficult to discriminate between latent TB or remission from TB [43].

In conclusion, the use of the ALS specimens with the standard ELISA technique holds potential as a future TB-specific diagnostic test. With the extensive availability of ELISA technology in developing country settings, this method should be applicable both in developing countries endemic for TB as well as industrialized countries for screening of suspected patients. Since this method does not require specimen from the site of disease, it should also be useful in diagnosis of paucibacillary childhood TB.

References cited herein are listed below for convenience.
1. WHO report 1999. Global Tuberculosis Control: Communicable Diseases, WHO. Geneva: World Health Organization, 1999.
2. Director General (DG) Health Services: Report on the national prevalence survey on tuberculosis in Bangladesh, 1987-88. Dhaka: Dhaka: Ministry of Health and Family Welfare. 1989.
3. Kumaresan J A R M, Murray C J L. Tuberculosis. In: Murray C L J L A, ed. Global Health Statistics—global burden of disease and injury series. Vol. 2. Boston, Mass.: Harvard University press, 1996:142-7.
4. Global Tuberculosis Control: Surveillance, Planning, Financing. In: Organization WH, ed. WHO Report 2002: Geneva, Switzerland, 2002.
5. Surveillance for multidrug resistant *Mycobacterium tuberculosis.* 2001-2002. ICDDR,B: Health and Science Bulletin. Vol. 1, 2002:6-10.
6. Ameglio F, Giannarelli D, Cordiali-Fei P, et al. Use of discriminant analysis to assess disease activity in pulmonary tuberculosis with a panel of specific and nonspecific serum markers. Am J Clin Pathol 1994;101:719-25.
7. Saltini C, Colizzi V. Soluble immunological markers of disease activity in tuberculosis. Eur Respir J 1999;14:485-6.
8. Kothadia S N, Deshmukh S and Saoji A M. Evaluation of direct microscopy as a screening test in the diagnosis of pulmonary tuberculosis. Indian J Pathol Microbiol 1990; 33:68-73.
9. Pottumarthy S M A, Harrison A C, Wells V C. Evaluation of the tuberculin gamma interferon assay: potential to replace the Montoux skin test. J CLin Microbiol 1999;37 (10):3229-32.
10. al-Hajjaj M S, Gad-el-Rab M O, al-Orainey I O and al-Kassimi F A. Improved sensitivity for detection of tuberculosis cases by a modified Anda-TB ELISA test. Tuber Lung Dis 1999;79:181-5.
11. Yilmaz A, Ece F, Bayramgurler B, Akkaya E and Baran R. The value of Ca 125 in the evaluation of tuberculosis activity. Respir Med 2001;95:666-9.
12. Huebner R E S M, Bass J B. The tuberculin skin test. Clin Infect Dis 1993;17:968-75.
13. Donald P R. Childhood tuberculosis. Curr Opin Pulm Med 2000;6:187-92.
14. Fine P E, Sterne J A, Ponnighaus J M and Rees R J. Delayed-type hypersensitivity, mycobacterial vaccines and protective immunity. Lancet 1994;344: 1245-9.
15. Dhand R, Ganguly N K, Vaishnavi C, Gilhotra R and Malik S K. False-positive reactions with enzyme-linked immunosorbent assay of *Mycobacterium tuberculosis* antigens in pleural fluid. J Med Microbiol 1988;26:241-3.
16. Wang C R, Liu M F, Chen M Y, Lin T P, Cheng C S and Chuang C Y. Enzyme-linked immunosorbent assay with BCG sonicate antigen for diagnostic potential of mycobacterial infection in Taiwan. Zhonghua Min Guo Wei Sheng Wu Ji Mian Yi Xue Za Zhi 1989;22:97-104.
17. Aoki A, Hagiwara E, Shirai A, et al. [Their titers and recognized molecules of IgG class anti-BCG antibody in sera from patients with tuberculosis]. Nihon Kyobu Shikkan Gakkai Zasshi 1990;28:729-35.
18. Banchuin N, Wongwajana S, Pumprueg U and Jearanaisilavong J. Value of an ELISA for mycobacterial antigen detection as a routine diagnostic test of pulmonary tuberculosis. Asian Pac J Allergy Immunol 1990;8:5-11.
19. Lu C Z, Qiao J, Shen T and Link H. Early diagnosis of tuberculous meningitis by detection of anti-BCG secreting cells in cerebrospinal fluid. Lancet 1990;336:10-3.
20. Arend S M A P, Meijgaarden K E V, Skojot R L V, Subronto Y W, Dissel J T V, Ottenhoff T H M. Detection of active tuberculosis infection by T cell responses to early-secreted antigenic target 6-kDa protein and culture filtrate protein 10. J Infect Dis 2000; 181:1850-4.
21. Doherty M L, Cassidy J P. New perspectives on bovine tuberculosis. Vet J 2002;163:109-10.
22. Pollock J M, Andersen P. The potential of the ESAT-6 antigen secreted by virulent mycobacteria for specific diagnosis of tuberculosis. J Infect Dis 1997;175:1251-4.
23. van Pinxteren L A H R P, Affer E M, Pollock J, Andersen P. Diagnosis of tuberculosis based on the two specific antigens ESAT-6 and CFP10. Clin Diagnos Lab Immunol 2000;7:155-60.

24. Querol J M, Oltra C, Granda D, et al. [Usefulness of IgG and IgM detection against antigen 60 in the diagnosis of thoracic tuberculosis]. An Med Intema 1993; 10:271-4.

25. Qadri S M, Smith K K. Nonspecificity of the Anda A60-tb ELISA test for serodiagnosis of mycobacterial disease. Can J Microbiol 1992;38:804-6.

26. Maes R F. Evaluation of the avidity of IgG anti-mycobacterial antibodies in tuberculous patients serum by an A-60 immunoassay. Eur J Epidemiol 1991;7:188-90.

27. Delacourt C, Gobin J, Gaillard J L, de Blic J, Veron M and Scheinmann P. Value of ELISA using antigen 60 for the diagnosis of tuberculosis in children. Chest 1993;104:393-8.

28. Turneer M, Van Nerom E, Nyabenda J, Waelbroeck A, Duvivier A and Toppet M. Determination of humoral immunoglobulins M and G directed against mycobacterial antigen 60 failed to diagnose primary tuberculosis and mycobacterial adenitis in children. Am.J Respir Crit Care Med 1994;150:1508-12.

29. Vekemans J, Lienhardt C, Sillah J S, et al. Tuberculosis contacts but not patients have higher gamma interferon responses to ESAT-6 than do community controls in The Gambia. Infect Immun 2001;69:6554-7.

30. Lyashchenko K, Colangeli R, Houde M, Al-Jahdali H, Menzies D and Gennaro M L. Heterogeneous antibody responses in tuberculosis. Infect Immun 1998;66:3936-40.

31. Daniel T. Immunodiagnosis of tuberculosis. In: S G, ed. Tuberculosis. Boston: Little Brown and Company, 1996: 223-33

32. Noordhoek G T, Arend H J K, Bjune G, et al. Sensitivity and specificity of PCR for detection of Mycobacterium tuberculosis: a blind comparison study among seven laboratories. J Clin. Microb. 1994;32:277-84.

33. Chang H S, Sack D A. Development of a novel in vitro assay (ALS assay) for evaluation of vaccine-induced antibody secretion from circulating mucosal lymphocytes. Clin Diagn Lab Immunol 2001;8:482-8.

34. Organization W H. Global tuberculosis control, 1999. WHO/CDS/TB/2000.275. Geneva, Switzerland.: World Health Organization, 2000

35. Fine P. Variation in protection by BCG: implications of end for heterologous immunity. Lancet 1995;346:1339-45.

36. Islam D W B, Ryd M, Lindberg A A, Christensson B. Immunoglobulin subclass distribution and dynamics of Shigella-specific antibody responses in serum and stool samples in shigellosis. Infect Immun 1995;63:2054-61.

37. Sousa A O W A, Poinsignon Y, Simonney N, Gerber F, Lavergne F, Herrmann J L, Lagrange P H. Kinetics of circulating antibodies, immune complex and specific antibody-secreting cells in tuberculosis patients during 6 months of antimicrobial therapy. Tubercle Lung Dis 2000; 80(1):27-33.

38. Andersen P, Munk M E, Pollock J M and Doherty T M. Specific immune-based diagnosis of tuberculosis. Lancet 2000;356:1099-104.

39. Johnson P D, Stuart R L, Grayson M L, et al. Tuberculin-purified protein derivative-, MPT-64- and ESAT-6-stimulated gamma interferon responses in medical students before and after Mycobacterium bovis BCG vaccination and in patients with tuberculosis. Clin Diagn Lab Immunol 1999;6:934-7.

40. Lein A D, von Reyn C F, Ravn P, Horsburgh C R, Jr., Alexander L N and Andersen P. Cellular immune responses to ESAT-6 discriminate between patients with pulmonary disease due to Mycobacterium avium complex and those with pulmonary disease due to Mycobacterium tuberculosis. Clin Diagn Lab Immunol 1999;6:606-9.

41. Ravn P, Demissie A, Eguale T, et al. Human T cell responses to the ESAT-6 antigen from Mycobacterium tuberculosis. J Infect Dis 1999;179:637-45.

42. Lalvani A, Nagvenkar P, Udwadia Z, et al. Enumeration of T cells specific for RD1-encoded antigens suggests a high prevalence of latent Mycobacterium tuberculosis infection in healthy urban Indians. J Infect Dis 2001;183:469-77.

43. Wu-Hsieh B A, Chen C-K, Chang J-H, et al. Long-lived immune response to early secretory antigenic target 6 in individuals who had recovered from tuberculosis. Clin Infect Dis 2001;33:1336-40.

44. Azim T, Islam M N, Bogaerts J, et al. Prevalence of HIV and syphilis among high-risk groups in Bangladesh. Aids 2000;14:210-1.

45. Azim T, Bogaerts J, Yirrell D L, et al. Injecting drug users in Bangladesh: prevalence of syphilis, hepatitis, HIV and HIV subtypes. Aids 2002;16:121-3.

We claim:

1. A method of diagnosing tuberculosis in a subject comprising culturing lymphocytes from said subject under suitable conditions such that antibodies are produced, and measuring the concentration of antibodies reactive with a tuberculosis antigen, wherein a statistically significant increase in said concentration over a normal control value is indicative of active tuberculosis infection.

2. The method of claim 1 wherein the lymphocytes are cultured for 1-5 days.

3. The method of claim 2 wherein the lymphocytes are cultured for 2-4 days.

4. The method of claim 1 wherein the lymphocytes are separated from other blood cells prior to culture.

5. The method of claim 1 wherein said antigen is selected from the group consisting of BCG, PPD, ESAT-6, LAM and CFP.

6. A method of diagnosing tuberculosis in a subject comprising:
   i) obtaining a blood sample from said subject;
   ii) separating lymphocytes from the sample;
   iii) culturing the lymphocytes in a culture medium under suitable conditions;
   iv) measuring the concentration of antibodies reactive with a tuberculosis antigen in said medium;
   wherein a statistically significant increase in said concentration over a normal control value, is indicative of active tuberculosis infection.

7. The method of claim 6 wherein said antigen is selected from the group consisting of BCG, PPD, ESAT-6, LAM and CFP.

8. The method of claim 1 wherein said antibodies are detected using ELISA or an immunochromatographic method.

9. The method of claim 1 wherein the concentration of antibody producing lymphocytes in the peripheral blood is measured using ELISPOT or by tagging the lymphocytes with a detectable marker.

10. The method of claim 9 wherein the detectable marker is a fluorescent labeled antibody.

* * * * *

UNITED STATES PATENT AND TRADEMARK OFFICE
CERTIFICATE OF CORRECTION

| | | |
|---|---|---|
| PATENT NO. | : 7,638,271 B2 | Page 1 of 1 |
| APPLICATION NO. | : 10/903855 | |
| DATED | : December 29, 2009 | |
| INVENTOR(S) | : David A. Sack | |

It is certified that error appears in the above-identified patent and that said Letters Patent is hereby corrected as shown below:

Title page:

Please correct the following:

Item (75) should read Inventor: David A. Sack, Timonium, MD (US)

Signed and Sealed this

Thirteenth Day of April, 2010

David J. Kappos
*Director of the United States Patent and Trademark Office*

UNITED STATES PATENT AND TRADEMARK OFFICE
CERTIFICATE OF CORRECTION

PATENT NO.         : 7,638,271 B2                                   Page 1 of 1
APPLICATION NO.    : 10/903855
DATED              : December 29, 2009
INVENTOR(S)        : David A. Sack and Rubhana Raqib It is certified that error appears in the above-identified patent and that said Letters Patent is hereby corrected as shown below:

Title page:

Please correct the following:

Item (75) should read Inventors: David A. Sack, Timonium, MD (US)
                                Rubhana Raqib, Mohakhali Dhaka (BD)

This certificate supersedes the Certificate of Correction issued April 13, 2010.

Signed and Sealed this

Eighteenth Day of May, 2010

David J. Kappos
*Director of the United States Patent and Trademark Office*